(12) United States Patent
Fuhr et al.

(10) Patent No.: US 6,610,188 B1
(45) Date of Patent: Aug. 26, 2003

(54) ELECTRODE ARRAY FOR FIELD CAGES

(75) Inventors: Günter Fuhr, Berlin (DE); Thomas Schnelle, Berlin (DE); Stefan Fiedler, Berlin (DE); Stephen Graham Shirley, Warks (GB)

(73) Assignee: Evotec Biosystems AG, Hamburg (DE)

( * ) Notice: Subject to any disclaimer, the term of this patent is extended or adjusted under 35 U.S.C. 154(b) by 0 days.

(21) Appl. No.: 09/308,841

(22) PCT Filed: Dec. 12, 1997

(86) PCT No.: PCT/EP97/07002

§ 371 (c)(1),
(2), (4) Date: Jul. 30, 1999

(87) PCT Pub. No.: WO98/28405

PCT Pub. Date: Jul. 2, 1998

(30) Foreign Application Priority Data

Dec. 20, 1996 (DE) .......................................... 196 53 659

(51) Int. Cl.[7] .............................................. G01N 27/26
(52) U.S. Cl. ...................... 204/643; 204/600; 204/450; 204/547
(58) Field of Search ................................ 204/547, 643, 204/450, 600

(56) References Cited

U.S. PATENT DOCUMENTS

| 4,164,460 A | 8/1979 | Jordan et al. |
| 4,326,934 A | 4/1982 | Pohl |
| 4,390,403 A | 6/1983 | Batchelder |
| 5,084,157 A | 1/1992 | Clark et al. |
| 6,056,861 A | * 5/2000 | Fuhr et al. .................. 204/547 |
| 6,149,789 A | * 11/2000 | Benecke et al. ............ 204/547 |

FOREIGN PATENT DOCUMENTS

| DE | 4034697 | 5/1992 |
| DE | 19500660 | 6/1996 |
| DE | 19500683 | 6/1996 |
| WO | 22583 | 10/1994 |

OTHER PUBLICATIONS

Sensors and Materials, vol. 7, No. 2 (1995) p. 131–146.
Microsystem Technologies 2 (1995) p. 1–7.
Contents of U. Zimmermann et al. in "Electromanipulation of Cells" CRC, (1996) Table of Contents only.

* cited by examiner

Primary Examiner—Nam Nguyen
Assistant Examiner—Kaj K. Olsen
(74) Attorney, Agent, or Firm—Birch, Stewart, Kolasch & Birch, LLP

(57) ABSTRACT

An electrode configuration for field cages, especially in microsystems, comprises a large number of electrodes in which an electrical potential can be applied to each end region through a feed region. The end region is arranged to form the field cage and inhomogeneous shielding fields outside the field cage. To reduce thermal convection, the feed region has a strip form whose width is substantially smaller than characteristic dimensions of the end region.

6 Claims, 3 Drawing Sheets

ELECTRODE ARRAY FOR FIELD CAGES

This application is the national phase under 35 U.S.C. §371 of PCT International Application No. PCT/EP97/07002 which has an International filing date of Dec. 12, 1997 which designated the United States of America.

BACKGROUND OF THE INVENTION

1. Field of the Invention

The invention concerns electrode configurations for forming field cages, used especially in Microsystems for handling and manipulating particles, and field cage electrodes for use in such electrode configurations.

2. Description of the Related Art

To produce certain states or for the operation of certain processes in numerous biotechnical, medical, gene engineering and chemical engineering systems, it is necessary to hold microscopic particles precisely in free suspensions or to move them in a predetermined manner. The particles of interest include biological cells or parts of them, latex particles or other socalled microbeads. By the influence of electrical fields in socalled field cages the particles are moved ("open" field cages) or held ("closed" field cages) in the suspension. In a held state the particles can be measured, for example, or caused to interact with one another (cf U. Zimmermann et al. in "Electromanipulation of Cells" in CRC, 1996, chapter 5, pp 259–328).

The fields for influencing the particles are formed of electrodes, preferably fabricated by semiconductor technology methods. To form a field cage, a plurality of electrodes are configured either two- or three-dimensionally and potentials are applied to them so that, in the space enclosed by the electrodes (the socalled inner space), a field distribution is created in which a particle can be trapped or moved in a particular direction.

The electrode shape and configurations for microsystem applications were only optimized to date in terms of the effectiveness of cage formation in the inner space (cf S. Fiedler et al. in "Microsystem Technology" 2, 1–7, 1995). It is known, for example, that electrodes can be formed with a strip form tapering hyperbolically into the inner space for field cages of several micrometers to several hundred micrometers. Such simple electrodes were regarded to date as optimal in terms of field cage formation and their optimization through relatively simple computation of the field gradients. Nevertheless, the following effect is a disadvantage in conventional electrode configurations and shapes.

If the particle density in a liquid (suspension) is low, single particles, eg a cell, can be held stably in the field cage for a long period (minutes to hours). At higher particle densities however, further particles enter the field cage in the course of time, which is generally undesirable. This effect is initially surprising, because the field cage represents a potential barrier intended to prevent migration of particles into the inner space. But there are extra forces present, directed towards the inner space, that allow the particles to overcome the potential. These forces are the result of thermal convection, especially warmup near the electrodes.

As a result of this effect, the use of field cages in microsystems is restricted to relatively small particle densities, which are frequently unacceptable in practical terms.

SUMMARY OF THE INVENTION

The object of the invention is to present an improved electrode configuration for cage formation and improved field cage electrodes for such an electrode configuration, with which larger particle concentrations can be processed, with greater stability and reliability, than with conventional Microsystems.

This object is solved by an electrode configuration and a field cage electrode of the present invention.

The invention is based on the idea of creating new electrode forms and configurations that, on the one hand, reduce or suppress thermal convection flows and, on the other hand, enhance the effectiveness of the potential barrier surrounding the field cage. Electrode configurations according to the invention consist of a large number of field cage electrodes, each with an end or head region to which electrical potential can be applied through a feed region. Unlike conventional electrode forms with smooth, uniform edges, the end regions of the electrodes in the invention are shaped so that highly inhomogeneous fields are created in both the inner space (field cage) and the outer space. Here the inhomogeneity of the fields is so strong, or the field gradients so pronounced, that a shielding (or screening) field forms outside the field cage. The shielding field should be strong enough for forces to act on the particles that compensate for the forces directed inwards (eg through thermal convection). For this purpose the end region of an electrode exhibits electrode segments that, in part at least, are limited by straight or slightly curved edges that abut against one another at predetermined angles. The edges abut against one another in such a way that an discontinous demarcation (formation of a corner or tip or the like) results. This means that high field line concentrations form on the edges of the end region, producing the required, large field gradients.

In a preferred embodiment of the invention, in addition to the above shaping of the end region to create inhomogeneous shielding fields, the feed region, through which the end region is connected to an electrode terminal, has an electrode surface as small as possible. Preferably the feed region is of strip form with a width optimized for the electrical power. The formation of feed regions that are as narrow as possible leads to a reduction of thermal convection.

The invention, unlike the electrode forms used to date and optimized for field cage creation, produces instead electrodes whose end regions allow the formation of field line concentrations, eg on edges or tips of the electrodes.

Electrode configurations according to the invention can be arranged planar two-dimensionally, the holding or moving of particles then being produced by interaction of the field cage with parts of the microsystem (mechanical limiting). Alternatively the electrode configurations may take on a three-dimensional form in which the particles are only held in the field cages by the effect of the electrical forces. But in the case of three-dimensional systems too, mechanical limiting can cooperate with the field cages.

In a special embodiment of the invention, not only the end regions of the electrodes but also the feed regions are provided with electrode segments that enable the formation of strong field gradients. With suitably designed interaction of adjacent field cage electrodes in particular, this allows open and closed field cages to be combined, eg in the form of a field cage with a feed channel.

Methods and devices according to the invention can be used in correlation spectroscopy, especially for verifying fluorescent molecules on the surface of submicrometer or micrometer particles and/or cells, or in pharmacological, medical diagnostic and/or evolutionary biotechnical applications. In particular, fluorescence correlation spectroscopy (WO 94/16313) and other, especially confocal fluorescence techniques, as proposed in WO 96/13744 and European patent application 96116373.0, can be used as verification methods. The last mentioned application suggests a method for analyzing samples by repeated measurement of the number of photons per predetermined time interval of electromagnetic radiation, especially light, emitted, scattered and/or reflected by particles in the sample, and determination of the distribution of the number of photons in the particular time intervals, whereby the distribution of the molecular intensities of the particles is found from the distribution of the number of photons.

BRIEF DESCRIPTION OF THE DRAWINGS

Embodiments of the invention will be described below with reference to the attached drawings. These show.

In what follows, embodiments of the invention are characterized in detail. A skilled person will see that features named in connection with certain embodiments can be implemented in other embodiments. There is no restriction to particular combinations of electrode geometries or configurations.

DETAILED DESCRIPTION OF THE INVENTION

Detailed description of the invention is set forth in the following discussion of the preferred embodiments. A skilled person will see that features named in connection with certain embodiments can be implemented in other embodiments. There is no restriction to particular combinations of electrode geometries or configurations.

Depending on the application the electrode configuration shown can have a characteristic size in the region of 1 µm to 500 µm or larger. The electrode configuration is best created with planar semiconductor technology on a chip and provided with suitable suspension feeds and sealing from its surroundings.

Figure 1:
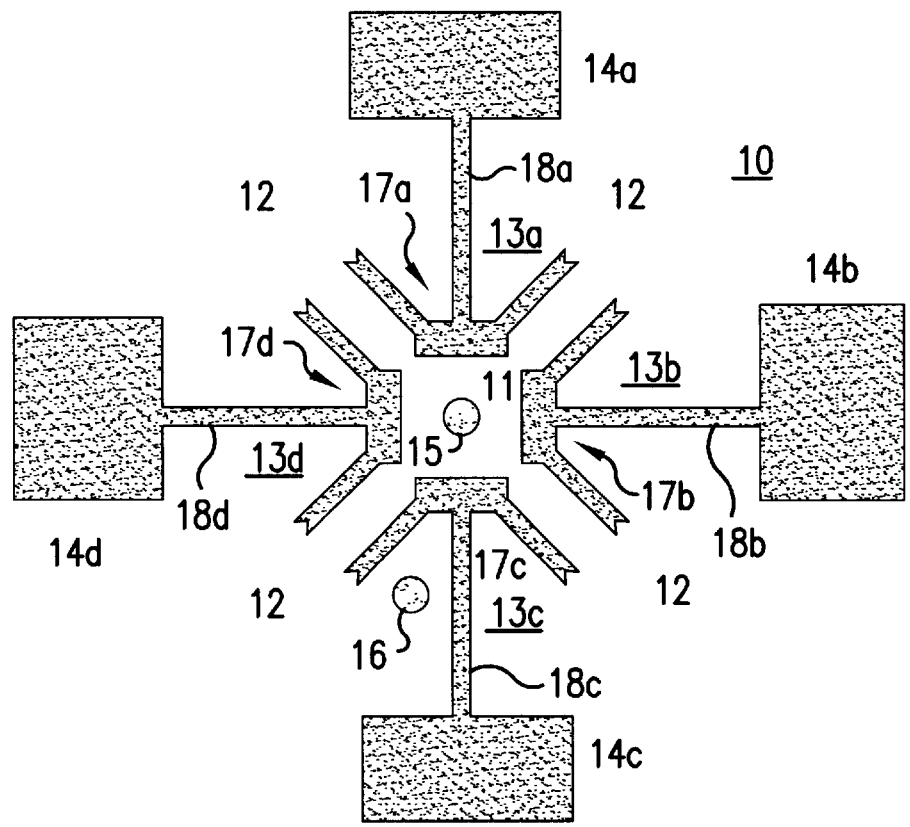
FIG. 1 shows a schematic plan view of a planar electrode configuration according to a first embodiment of the invention.

As an alternative to the planar electrode configuration shown in FIG. 1, it is also possible to create a three-dimensional field cage. This is achieved with an electrode configuration according to FIG. 2 consisting of two sub-electrode configurations 21a, 21b, each of which essentially corresponding to the electrode configuration of FIG. 1. Between the sub-electrode configurations, created on a silicon or glass substrate for example, there is enclosed a suspension layer 22 with the particles that are to be manipulated (trapped).

Figures 3A, 3B:
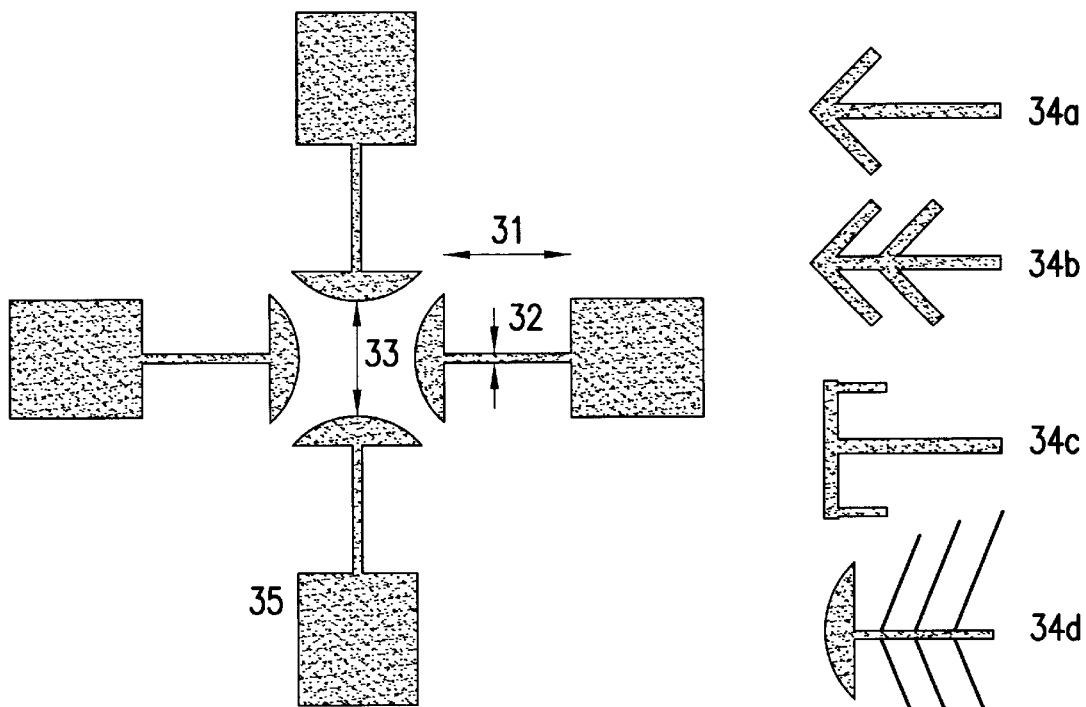

Further examples of electrodes embodying the invention are shown in FIGS. 3A and 3B. The planar electrode configuration according to FIG. 3A matches for the most part the electrode configuration of FIG. 1, the electrode end regions not being arrow-shaped however but taking the form of a semicircle. These semicircle segments forming the end regions extend in directions that are perpendicular on a line connecting the center of the inner space and the electrode terminal. In other words, if the inner space is separated by reference planes from the particular electrodes, the end region of each electrode extends in a direction on a parallel plane to the reference plane.

For effective retaining of particles from the outer space and suppression of thermal convection flow, the spacing 31 between the electrode terminal and the end region (ie the length of the feed region) should correspond at least to the spacing 33 between two opposite electrodes of the electrode configuration. Furthermore, it is preferred if the width 32 of the feed region is smaller than or equal to one quarter of the spacing 33. The electrode terminals, formed by feeders, present no restrictions in terms of width and length. It is preferred however, to reduce electrical losses, if the electrode terminals 35 are provided with insulating layers. These should be between about 50 nm and several µm in thickness.

The narrow design of the feed region 35 presents the following advantage. A wide strip electrode means that a particle in the particle suspension is exposed to a, for the most part, homogeneous electrical field in which it can easily be shifted laterally, ie in the direction of the field cage too, by a suspension flow. This disadvantage of wide electrode strips is overcome by the implementation of narrow electrode segments according to the invention.

In addition to the feed region, the end regions of the field cage electrodes can also be implemented with narrow strips, as exemplified by FIG. 3B in the case of the end regions 34a–34d (arrow shape, dual arrow shape, T profile, "antenna" shape).

Figure 2:
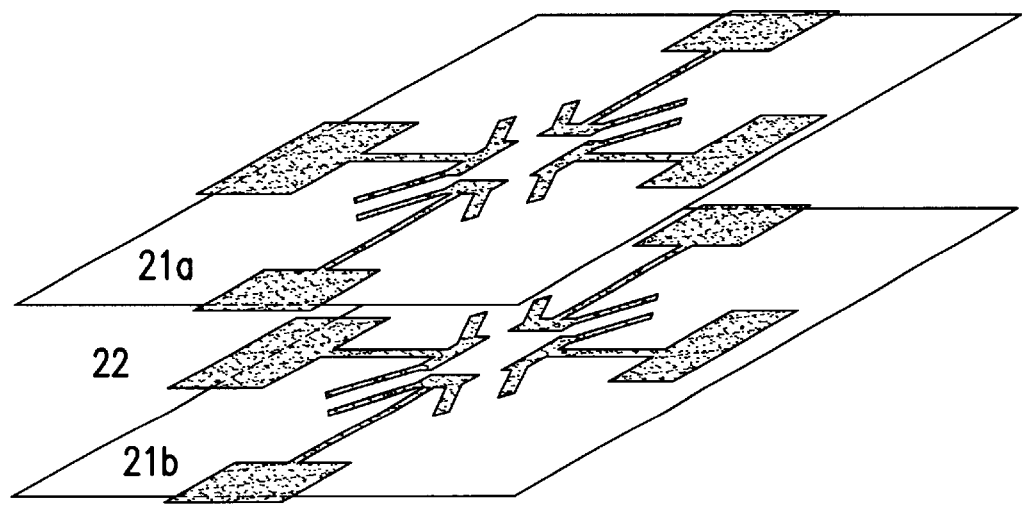
FIG. 2 shows a schematic perspective of an electrode configuration consisting of two electrode configuration consisting of two electrode configuration according to FIG. 1, FIGS. 3A and 3B show a further embodiment of an electrode configuration according to the invention and field cage electrodes shaped according to the invention.

The electrode configurations in FIG. 1 through FIG. 3 comprise between four and eight identical electrodes. But it is also possible to implement the invention with a different number of electrodes and different electrode designs within one electrode configuration. A field cage configuration in a microsystem comprises in the widest sense (possibly in conjunction with mechanical means of limiting) at least one field cage electrode with which a suspended particle is manipulated. If a plurality of electrodes are used, these are arranged as symmetrically as possible in relation to the inner space in which the cage is formed. A square, regular multi-sided or circular arrangement is possible for example. But asymmetrical arrangements are also conceivable.

Figure 4A:
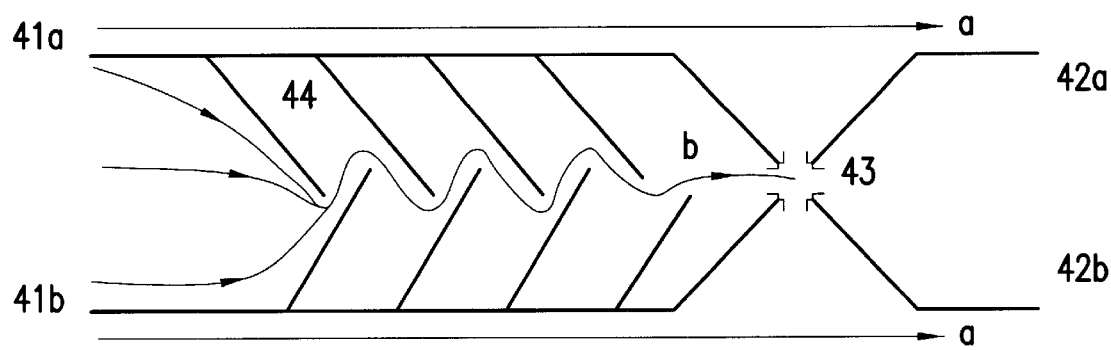
FIGS. 4A and 4B show schematic plan views of electrode configurations in which open and clos3ed field cages according to the invention, are combined.
Figure 4B:
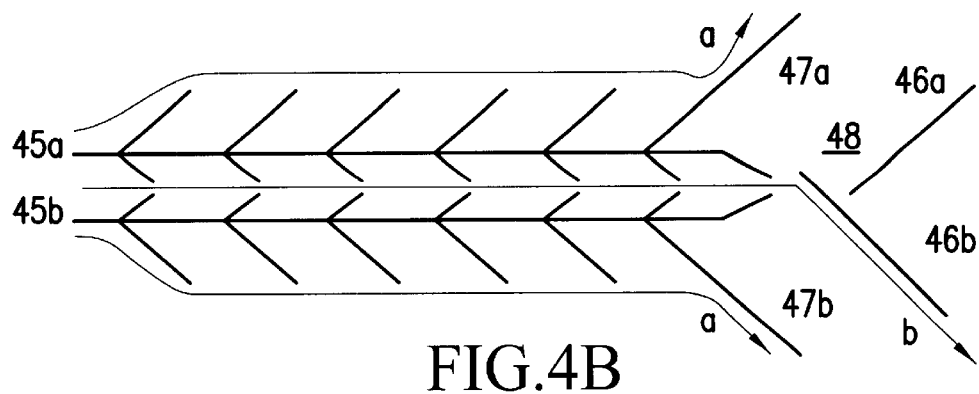

FIGS. 4A and 4B illustrate microsystems comprising a combination of a field cage electrodes (FIG. 4A), or a sorting device 48, here meant to be an open field cage, with a feed channel (FIG. 4B). The FIGS. 4A and 4B each show one half of the respective microsystem. The entire system is formed of a structural element with the illustrated electrode configuration and a second structural element with an identical counter-electrode configuration as a mirror image. Both structural elements are exactly aligned using spacers with the structured surfaces facing one another. The particle suspension flows through the space between the two structural elements. This space (ie the vertical interval between the electrode configurations) is about as large as the field cage 432 is wide.

According to FIG. 4A, two field cage electrodes of the field cage 43 have a modified design of the feed regions 41a and 41b, which themselves form field cage electrodes for an open field cage. The feed regions form a feed channel that conducts particles in a predetermined manner along the path b to the field cage 43. But particles on the paths a are conducted past the field cage 43 (extra mechanical means of separation, not shown, can be provided for this purpose). For controlled conducting of the particles to the field cage 43, the feed regions 41a and 41b are each provided with strip electrodes 44 directed in herringbone fashion to the middle of the feed channel to form electrode end regions.

Conduction of the particles through the feed channel is obtained by predetermined driving of the feed regions and the electrodes 41a, 41b, 42a, 42b and the corresponding counter-electrodes (not shown) in the overall system. All electrodes are driven by an appropriately selected alternating potential of the frequency f, the following phase shift being implemented for a specific particle conduction between the electrodes (and corresponding counter-electrode Γ) 41a: 0° Γ,: 180°, 41b: 180°; Γ: 0°; 42a: 180°,: Γ; 42b: 0° and: Γ180°. The potential amplitudes should be between 0.1 and 100 V and can be selected by a skilled person as a function of the particular application.

In FIG. 4B a feed channel, formed by the electrodes 45a and 45b, conducts particles along the path b to a sorting device 48 with the electrodes 46a and 46b. Here the feed channel to the sorting device itself forms an open field cage in which the electrodes are provided with electrode segments intended to produce strong field inhomogeneities. The electrode segments 47a and 47b are additionally provided to deflect particles along the paths a.

For the conduction of particles there are again four electrodes 45a, 45b, 46a, 46b and the corresponding counter-electrodes (Γ, not shown). The path b is implemented by applying alternating potentials to the electrodes 45a, 45b, 46b, and leaving the electrode 46a, floating, and likewise for the corresponding counter electrodes. The set phase relationships are: 45a: 0°,Γ: 180°; 45b: 180°, Γ: 0°; 46b: 0°, Γ: 180°. If the particles are not to be conducted on the path b (shown) but past the electrode 46a, the electrode 46b, would be floating and the electrode 46a, 180°. For corresponding counter-electrodes, the corresponding counter-electrode for electrode 46a would be 0°.

The invention also concerns a method for handling the described electrode configurations, especially for incorporating particles in field cages. The introduction of one or more particles for manipulation is characterized by the fact that a suspension flow is conducted through the electrode configuration while this is driven so that particles conducted by the suspension are retained. In an electrode configuration according to FIG. 1 for example, the suspension is conducted in a direction running from bottom left to top right. Here the adjacent electrode segments of the electrode end regions 17d and 17c, 17a and 17b (possibly in conjunction with additional electrode segments for a three-dimensional configuration according to FIG. 2) form a channel through which the suspension is conducted. During this flow the electrodes 13a and 13b are driven so that particles conducted by the flow come up against a potential barrier. At the same time the electrodes 13c and 13d are switched off. As soon as a particle is detected in the inner space 11, by an optical device for example, the electrodes 13c and 13d are switched on again to close the field cage and shield any following particles. A special advantage of the electrode configuration and the method according to the invention is that this screening of any following particles is very effective due to the immediate formation of inhomogeneous shielding fields.

Typical drive protocols for the manipulation of living cells suspended in physiological solutions and for 3 to 100 μm large beads (latex, sephadex, etc) are:

| Cells (concrete: animal fibroblasts, 15 μm diameter) | |
| --- | --- |
| Drive amplitude | 2.5 to 8 V |
| Useful frequency | 1 MHz to 1 GHz (usually 5 or 10 MHz) |
| Signal characteristic | sinusoidal, squarewave |
| Switching speed for cutting electrodes in and out | 1 us to 1 s |
| Duration of field application | 1 ms to min |

Functional ability of basic elements as function of flow velocity of solution in system:
Herringbone system (FIGS. 4A, 4B) up to 400 μm/s
Field cage (FIGS. 1, 2, 3) 50 to 100 μm/s
Diplexer (FIG. 4B, 46a, 46b) up to 1000 μm/s

| Microbeads (concrete: latex, 15 μm diameter) | |
| --- | --- |
| Drive amplitude | 2.5 to 15 V |
| Useful frequency | 10 kHz to 100 MHz (usually 100 kHz to 1 MHz) |
| Signal characteristic | sinusoidal, squarewave |
| Switching speed for cutting electrodes in and out | 1 us to 1 s |
| Duration of field application | 1 ms to min |

Functional ability of basic elements as function of flow velocity of solution in system:
Herringbone system (FIGS. 4A, 4B) up to 2000 μm/s
Field cage (FIGS. 1, 2, 3) up to 80 μm/s
Diplexer (FIGS0. 4B, 46a, 46b) up to 2000 μm/s The method exemplified above with reference to FIG. 1 can also be implemented in other electrode configurations and geometries by the same principle, the electrodes being driven in a two-step procedure so that first a potential barrier is formed across the suspension flow and then, as soon as the particle or particles are in the inner space, the field cage is closed.

The electrode configurations and method according to the invention can be used to measure, manipulate, concentrate, aggregate, immobilize, characterize or identify microparticles, cells, viruses, macromolecules and other fluid or solid bodies of a size from 1 nm to 500 μm.

Figure 5:
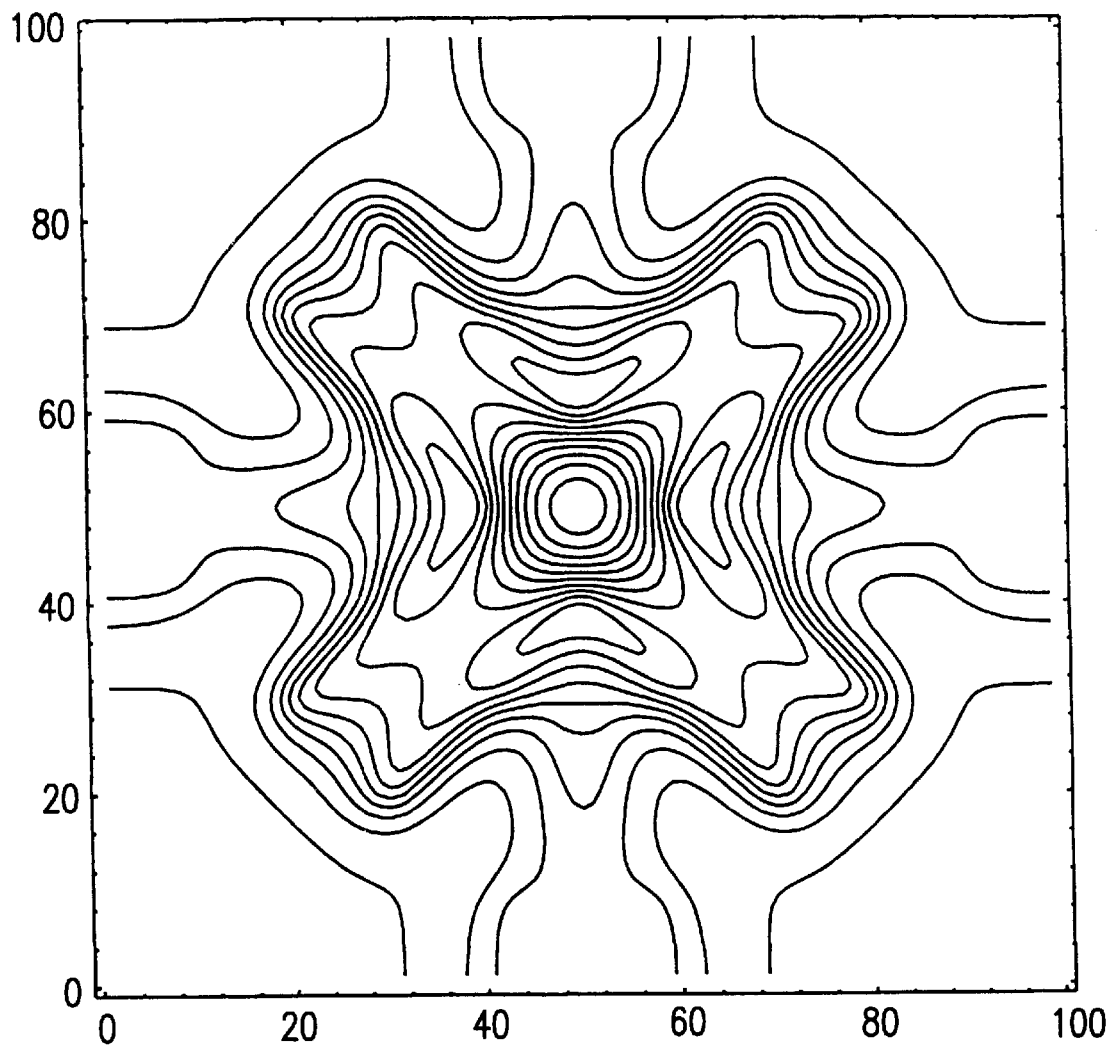
FIG. 5 shows a typical characteristic of field lines.

FIG. 5 shows an example of field lines in a field cage formed according to the invention on the basis of a modified arrow-shaped electrode configuration. These are the equipotential lines ($E^2$rms, averaged with time), ie the potential for the dielectrophoretic force. Very noticeable is the asymmetrical field distribution in the cage and outside as well as the basic arrow-shaped electrode form.

What is claimed is:
1. Electrode configuration, comprising:
a plurality of electrodes surrounding an inner space which can be filled with a suspension and being arranged to create a field cage in the inner space, each of said electrodes having a feed region and an end region, wherein each feed region is arranged for applying an electrical potential to the corresponding end region for creating field gradients in the inner space; and
strip-shaped electrode segments which are connected to each end region of said electrodes, wherein said electrode segments form an arrow shape or a T-shape with rectangular extending strips with the ends of the electrode segments being directed opposite to the inner space and wherein said electrode segments are adapted to form inhomogeneous shielding fields outside the inner space that create field gradients repelling particles in the suspension away from the field cage in the inner space.

2. Electrode configuration, comprising:

a plurality of electrodes surrounding an inner space which can be filled with a suspension and being arranged to create a field cage in the inner space, each of said electrodes having a feed region and an end region, wherein each feed region is arranged for applying an electrical potential to the corresponding end region for creating field gradients in the inner space and each end region comprises a semicircle section shaped electrode segment at the tip of the end region; and strip-shaped electrode segments which are connected to each end region of said electrodes, wherein said electrode segments form an arrow shape with the ends of the electrode segments being directed away from the inner space and wherein said electrode segments are adapted to form inhomogeneous shielding fields outside the field cage that create field gradients repelling particles in the suspension away from the field cage.

3. Electrode configuration according to claim 1 or 2, wherein each feed region is formed by an electrode strip whose width is less than or equal to one quarter of a spacing between the electrodes in the inner space in which the field cage is formed.

4. Electrode configuration according to claim 1 or 2, wherein at least two electrodes are arranged so that the feed regions thereof form a feed channel-being capable to conduct particles on a predetermined path to the field cage.

5. Electrode configuration according to claim 4, wherein the feed regions forming said feed channel comprise a plurality of strip electrodes.

6. Electrode configuration according to claim 5, wherein the plurality of strip electrodes form a fishbone-like strip pattern pointing into the feed channel.

* * * * *

UNITED STATES PATENT AND TRADEMARK OFFICE
CERTIFICATE OF CORRECTION

PATENT NO.    : 6,610,188 B1
DATED         : August 26, 2003
INVENTOR(S)   : Fuhr et al.

It is certified that error appears in the above-identified patent and that said Letters Patent is hereby corrected as shown below:

<u>Title page,</u>
Item [54], Title, please correct to read as follows:
-- ELECTRODE CONFIGURATION FOR FIELD CAGES --
Item [73], Assignee, please correct to read as follows:
-- Evotec OAI AG --

Signed and Sealed this

Sixteenth Day of March, 2004

JON W. DUDAS
*Acting Director of the United States Patent and Trademark Office*